United States Patent [19]

Someya et al.

[11] Patent Number: 4,798,618
[45] Date of Patent: Jan. 17, 1989

[54] NOVEL CHLOROACETANILIDE DERIVATIVES AND HERBICIDES CONTAINING THE SAME FOR USE IN PADDY FIELD

[75] Inventors: Shinzo Someya, Tokorozawa; Rokuro Akahira, Tokyo; Hiroshi Horino, Yokohama; Michihiro Ohnaka, Yokohama; Takashi Kiuchi, Yokohama, all of Japan

[73] Assignee: Agro-Kanesho Co., Ltd., Tokyo, Japan

[21] Appl. No.: 447,651

[22] Filed: Dec. 7, 1982

[30] Foreign Application Priority Data

Dec. 10, 1981 [JP] Japan ................................. 56-199058
Oct. 12, 1982 [JP] Japan ................................. 56-178699

[51] Int. Cl.⁴ ..................... A01N 43/48; A01N 37/18
[52] U.S. Cl. .................................. 71/92; 71/118; 564/211; 564/271; 564/305
[58] Field of Search ............... 548/375; 564/112, 211; 71/92, 118

[56] References Cited

U.S. PATENT DOCUMENTS

| | | | |
|---|---|---|---|
| 3,442,945 | 5/1969 | Olin | 564/214 |
| 3,547,620 | 12/1970 | Olin | 71/118 |
| 4,258,196 | 3/1981 | Chapp et al. | 564/214 X |
| 4,284,564 | 8/1981 | Alt et al. | 564/214 X |
| 4,296,254 | 10/1981 | Middlebrook et al. | 564/211 X |
| 4,322,553 | 3/1982 | Chupp | 564/211 X |
| 4,345,938 | 8/1982 | Alt | 71/118 |
| 4,351,667 | 9/1982 | Chupp | 564/152 X |

FOREIGN PATENT DOCUMENTS

| | | |
|---|---|---|
| 48-4525 | 6/1973 | Japan. |
| 48-37820 | 6/1973 | Japan. |
| 581607 | 9/1976 | Switzerland ....................... 564/112 |

*Primary Examiner*—Robert V. Hines
*Attorney, Agent, or Firm*—McDermott Will & Emery

[57] ABSTRACT

Disclosed herein are novel chloroacetanilide derivatives which act as remarkably effective herbicides when sprayed in a paddy field, the chloroacetanilide derivatives being 2',6'-diethyl-N-[(cis-alkenyloxy)methyl]-2-chloroacetanilides [A] represented by the general formula

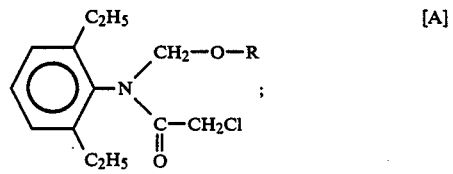

wherein R is a cis-form alkenyl group having 4 or 5 carbon atoms.

Also disclosed are herbicide compositions for use in a paddy field and containing at least one of said chloroacetanilide derivatives [A] and at least one pyrazole derivative [B] represented by the general formula

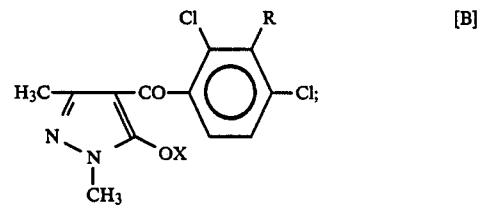

wherein R is a hydrogen atom or methyl group and X is a 4-toluenesulfonyl group or benzoylmethyl group; or-α-(2-naphtoxy)-propyonanilide [C] represented by the formula

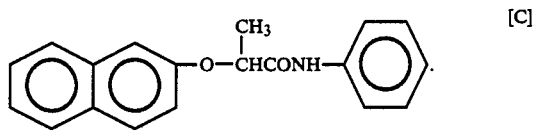

3 Claims, No Drawings

NOVEL CHLOROACETANILIDE DERIVATIVES AND HERBICIDES CONTAINING THE SAME FOR USE IN PADDY FIELD

The present invention relates to novel 2',6'-diethyl-N-[(cis-alkenyloxy)methyl]-2-chloroacetanilides, and to herbicides containing said novel chloroacetanilide derivatives for use in a paddy field.

More particularly, the present invention relates to 2',6'-diethyl-N-[(cis-alkenyloxy)methyl]-2-chloroacetanilides (hereinafter referred to as the compounds of this invention) represented by the general formula

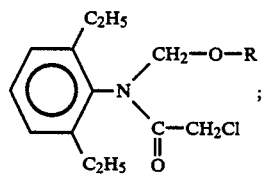

wherein R is a cis-form alkenyl group having 4 or 5 carbon atoms. The present invention also relates to a herbicide for use in a paddy field and containing, as an effective component, at least one of said compounds of this invention, and to a herbicidal composition containing, as effective components, at least one of said compounds of this invention and at least one pyrazole derivative [B] represented by the general formula

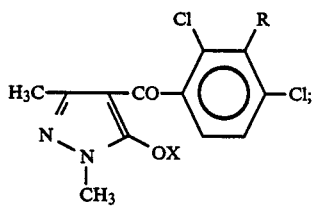

wherein R is a hydrogen atom or methyl group and X is a 4-toluenesulfonyl group or benzoylmethyl group; or α-(2-naphtoxy)-propionanilide [C] represented by the formula

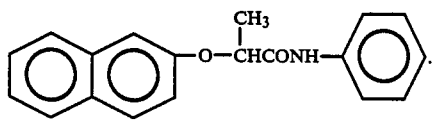

In the following description, the herbicide for use in a paddy field and comprising, in combination, the compounds [A] and [B] or the compounds [A] and [C] will be referred to as the herbicidal compositions of this invention.

An object of this invention is to provide the compounds [A] of this invention which may be used as active herbicidal components when sprayed in a paddy field.

Another object of this invention is to provide a herbicide for use in a paddy field and containing at least one of the compounds [A] of this invention.

A further object of this invention is to provide a herbicidal composition for use in a paddy field and containing at least one of the compounds [A] of this invention and at least one pyrazole derivative defined by the general formula [B] set forth hereinbefore.

A still further object of this invention is to provide a herbicidal composition for use in a paddy field and containing at least one of the compounds [A] of this invention and α-(2-naphtoxy)-propionanilide represented by the formula [C] set forth hereinbefore.

Other objects and advantages of this invention will become apparent from the following description.

Many haloacetanilide derivatives acting as herbicides have hitherto been known in the art, and N-alkoxymethyl derivatives thereof are also made known, for example, by Japanese Patent Publication Nos. 4524/1973 and 37820/1973 and by U.S.Pat. Nos. 3,442,945 and 3,547,620. Particularly, Japanese Patent Publication No. 37820/1973 referred to above discloses the results of tests conducted to examine the poisonous activities, against plants at pre-germination stage, of more than a hundred of haloacetanilide derivatives including N-alkenoxymethyl derivatives.

Amongst these known derivatives, commercially available compounds are 2',6'-diethyl-N-methoxymethyl-2-chloroacetanilide and 2',6'-diethyl-N-butoxymethy-2chloroacetanilide, both being represented by the aforementioned general formula [A] wherein R is an alkyl group shown by $C_1$ for the former compound and wherein R is an alkyl group shown by $C_4$ for the latter compound.

Amongst the haloacetanilide derivatives referred to above, it is considered that 2',6'-diethyl-N-alkoxymethyl-2-chloroacetanilides have particularly excellent herbicide activities. However, the actions of the N-alkoxymethyl derivatives on various plants are appreciably influenced by the difference of the included alkyl group. In fact, the N-methoxymethyl derivative ($R=C_1$) is used as a herbicide to be sprayed over a plowed field for cultivating corn, soybean, cotton or sugar cane, whereas the N-butoxymethyl derivative ($R=C_4$) is used as a herbicide to be sprayed in a paddy field for cultivating paddy field rice or sprayed over a field for cultivating wheat or sugar beet. Referring to Table 1 (showing the test results) of Japanese Patent Publication No. 37820/1973, the N-methoxymethyl derivative and the N-ethoxymethyl derivative hinder the growth of rice plant, but the N-propoxymethyl derivative and N-butoxymethyl derivative do not hinder the growth of rice plant. (Reference should be made to Compound Nos. 3, 8, 14 and 21.).

Even though the carbon number of the included group R are the same, the action of a derivative including a saturated alkyl group is different from the actions of the derivatives including unsaturated alkenyl or alkynyl groups. For example, the substituted product of N-propoxymethyl does not hinder the growth of rice plant, whereas the substituted products of N-propenyloxymethyl and N-propynyloxymethyl hinder the growth of rice plant. (Reference should be made to Compound Nos. 9, 11 and 21 of Table 1 referred to above.)

According to the conventional knowledge in the art, the analogous compounds including saturated alkoxy groups having 3 or more carbon atoms are effective herbicides when sprayed in a paddy field. On the other hand, the conventional knowledge teaches that the substituted products of alkenyloxy groups hinder the growth of rice plant even if the alkenyloxy groups have 3 or more carbon atoms.

However, in the course of examining the influence of the analogous compounds on the paddy field rice plant and the herbicide activity on *Eohinochloa crus-galli P. Beauv*, a representative of the significantly harmful weeds, when used as herbicides in a paddy field, surprising results have been found. Namely, we have found that the derivatives including alkenyloxy groups having 4 or 5 carbon atoms do not significantly hinder the growth of rice plant, and that the compounds including cis-form alkenyloxy groups are appreciably improved in herbicide effect and the harmful actions thereof on the paddy field rice plant (particularly under high temperature condition) and fishes are considerably depressed when compared to the trans-form alkenyloxy derivatives and other type of commercially available products, although the steric isomers thereof including the corresponding trans-form alkenyloxy groups are inferior to a compound including butoxy group in herbicide effect when used in a paddy field.

When the compounds of this invention are applied over the surface of water in a paddy field for cultivating paddy field rice particularly before the weeds have not yet sprouted, selective and strong herbicide actions on annual and perennial weeds including *Eohinoohloa crus-galli P. Beauv.* can be obtained while they do not adversely affect the growth of rice plant before and after implantation under a high or low temperature condition and they have higher safety factor to fishes.

The compounds of this invention include the following compounds:

(1) 2',6'-diethyl-N-[(2-cis-butenoxy)methyl]-2-chloroacetanilide
(2) 2',6'-diethyl-N- [(2-cis-pentenoxy)methyl]-2-chloroacetanilide
(3) 2',6'-diethyl-N- [(3-cis-pentenoxy)methyl]-2-chloroacetanilide
(4) 2',6'-diethyl-N-[(1-methyl-2-cis-butenoxy)methyl]-2-chloroacetanilide Amongst the aforementioned compounds, the compounds (1) and (2) are particularly recommendable.

The compounds of this invention are characterized by the fact that all of them are cis-form. Although it is preferred that the purity of the compound is as high as possible, the compounds may be contaminated with a small quantity of the by-product trans-isomer as far as the effect of this invention is not substantially impared. However, since the effect of this invention is gradually decreased as the content of contaminating trans-isomer increases, the content of the cis-isomer should be generally not lower than 70%, preferably not lower than 90%.

It is also essential that the compounds of this invention have the group R having 4 or 5 carbon atoms. If the carbon number of the included group R is 6 or more, the herbicide activity is lowered disadvantageously to the extreme degree.

The compounds of this invention may be prepared by various methods. Preferably, the compounds of this invention may be prepared by reacting 2',6'-diethyl-N-chloromethyl-2-chloroacetanilide with cis-alkenols in the presence or absence of an acid binder. The starting materials are the known compounds. 2',6'-Diethyl-N-chloromethyl-2-chloroacetanilide may be easily obtained by reacting 2,6-diethylaniline with formalin or an oligomer of formaldehyde to form an azomethine compound which is then reacted with chloroacetyl chloride. The cis-alkenols may be obtained by the partial hydrogenation of alkynols in the presence of a Lindlar or other type catalyst.

Alternatively, the compounds of this invention may be prepared by reacting 2,6-diethylaniline with cis-alkenyl-halomethyl-ethers to obtain N-(cis-alkenoxy) methyl-2,6-diethylanilines which are reached with chloroacetyl chloride, or by reacting N-chloroacetyl2,6-diethylaniline with cis-alkenyl-halomethyl-ethers in the presence of an acid binder.

According to a further aspect of this invention, at least one of the compounds of this invention is combined with other kinds of herbicide compounds to provide composite herbicide compositions which are effective to a variety of weeds.

In general, various weeds are co-exsisting and growing in the same area of a paddy field, and respective weeds sprout and grow at different times. For this reason, it is extremely difficult to wither all of these weeds by a one-time treatment of spraying a herbicide. In order to wither the weeds completely, a variety of herbicides should be sprayed at different growth stages of the weeds. If some weeds survive after the application of herbicide, they grow thick over the field together with the serotenously sprouting weeds or those reviving after once being withered, resulting in reduction of the effect obtainable by the application of herbicides.

Accordingly, there is an increasing demand for a safe herbicide which has high herbicide activities not only on weed seeds at the pre-sprouting stage but also on the growing weeds at the later stage and which can maintain its herbicide activity for an appreciable time period.

As has been described hereinbefore, we have found that the compounds of this invention represented by the general formula [A] are remarkably improved in herbicide effect and also reduced in chemical injury on the paddy field rice plant (particularly under a high temperature condition) and on fishes when sprayed in a paddy field, as compared to other type chloroacetanilide herbicides. However, the compounds [A] are not fully satisfactory when used singly, since the flexibility or adaptability thereof for withering a variety of weeds are restricted and the herbicide activity thereof is not sufficiently high and is not preserved for a prolonged period of time. For this reason, when the compounds of this invention are used singly, it is hardly possible to meet all of the aforementioned requirements for the herbicide.

After eager pursuits for overcoming the disadvantages of the compounds [A] of this invention and for obtaining a further improved herbicide, we have found that an appreciably excellent herbicide activity, not obtainable when used singly, can be obtained by using at least one of the compounds [A] in combination with a defined pyrazole derivative [B] or in combination with α-(2-naphtoxy)-propionanilide [C]. Particularly, when the aforementioned herbicidal composition is applied just before or after the implantation of paddy field rice plant at the early stage of growth of weeds, the herbicide activity of the composition can be preserved for a long period of time by one-time application and the need of subsequent herbicide treatment can be substantially eliminated.

In accordance with a further aspect of this invention, there is provided a herbicidal composition for use in a paddy field and containing, as effective components, at least one 2',6'-diethyl-N-[(cis-alkenyloxy) methyl]-2-chloroacetanilide represented by the general formula

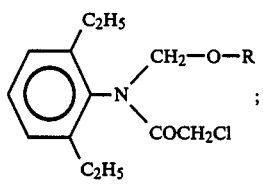

wherein R is a cis-form alkenyl group having 4 or 5 carbon atoms; and also containing at least one pyrazole derivative [B] represented by the general formula

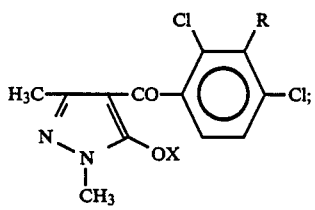

wherein R is a hydrogen atom or methyl group and X is a 4-toluenesulfonyl group or benzoylmethyl group or α-(2-naphtoxy)-propionanilide [C] represented by the

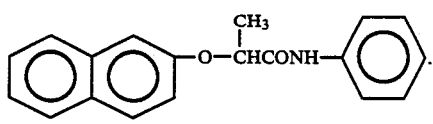

One of the effective components, the compound [A], included in the herbicidal composition for use in a paddy field according to this invention is a novel compound which has not been specifically disclosed in any prior art reference to our best knowledge, and preferred examples thereof are the following compounds:

[A] Chloroacetanilide Derivative

A-1: 2',6'-diethyl-N-[(2-cis-butenoxy)methyl]-2-chloroacetanilide
A-2: 2',6'-diethyl-N-[(2-cis-pentenoxy)methyl]-2-chloroacetanilide As aforementioned, these compounds may be prepared by any known synthesis processes for the preparation of chloroacetanilides. For example, these compounds may be prepared by reacting 2',6'-diethyl-N-chloromethyl-2-chloroacetanilide with cis-alkenols in the presence or absence of an acid binder.

The other effective components, the compounds [B] and [C] are the known compounds conventionally used as the herbicides for use in a paddy field, the representative examples being set forth as follows:

[B] Pyrazole Derivative

B-1: 1,3-dimethyl-4-(2,4-dichlorobenzoyl)-5-pyrazolyl-4-toluenesulfonate
B-2: 1,3-dimethyl-4-(2,4-dichlorobenzoyl)-5-phenacyloxypyrazole
B-3: 1,3-dimethyl-4-(2,4-dichloro-3-methyl-benzoyl)-5-phenacyloxypyrazole

[C] α-2-(naphtoxy)propionanilide

The compounds [B] set forth above have herbicide activities on annual Gramineae weeds, broadleaf weeds and perennial weeds, such as *Cyperus serotinus Rottb.*, *Sagittaria pygmaea Mig.* and *Sagittaria trifolia L.*, but the herbicide activities thereof are lowered, particularly the reduction in herbicide activities thereof on *Echinochloa crus-galli P. Beauv.* being particularly significant, if they applied at a later stage when the weeds have been grown beyond some extent.

The compound [C] exerts considerably high herbicide activity on annual and perennial broadleaf weeds, particularly on *Sagittaria pygmaea Mig.*, by the treatment when the weeds are at the early growth stage. However, this compound [C] has poor herbicide activity on Gramineae including *Echinochloa crus-galli P. Beauv.*, and hence there is left a problem by the single use thereof.

It has been a surprising finding that the herbicidal composition of this invention comprising at least one of the chloroacetanilide derivatives [A] in combination of at least one of the pyrazole derivatives [B] or α-(2-naphtoxy)-propionanilide [C] can be used to remove a variety of weeds beyond the range expected in view of the effective herbicide activities of the respective component compounds, the herbicide activities of the herbicidal composition of this invention being expanded so broad as to remove Gramineae, Cyperaceae plants, general broad leaf weeds and general perennial weeds, such as *Eleocharis acicularis Roem.*, *Scirpus hotarui Ohwi*, *Cyperus serotinus Rottb.* and *Sagitaria pygmae Mig.* It has been further found that satisfactory herbicide activity may be obtained by applying an extremely smaller quantity of the composite composition as being calculated from the herbicide activities of respective components when used singly while securing the safety for the paddy field rice plant. Moreover, sufficiently high herbicide activity can be obtained by a one-time treatment and can be preserved for a long period of time after the treatment.

When comparing to a herbicidal composition composed of commercially available 2',6'-diethyl-N-(butoxymethyl)-2-chloroacetanilide in combination with the pyrazole derivative [B]-1 or in combination with the compound [C], the herbicidal compositions of this invention are further improved in herbicide activities, reduction in chemical injury on paddy field rice plant (particularly under a high temperature condition) and on fishes.

The mixing ratio of the active compound [A] to the active compound [B] or [C], by parts by weight based on 100 parts by weight of the finished product of granule form, ranges generally within [A]:[B]=1-7:5-15 and [A]:[C]=1-7:5-15, and preferably [A]:[B]=2-4:6-8 and [A]:[C]=2-4:6-8.

Optimum dosage quantity of the herbicidal composition of this invention varies depending on the conditions of the atmosphere and soil, the kinds and densities of the weeds, the form of the composition, the time of dosage or application and the method of application. Although not specifically limited, the herbicidal composition of this invention is applied so that generally 50 to 600 grams, preferably 200 to 350 grams, of the active herbicide components are sprayed over ten ares of the field.

The herbicidal composition for use in a paddy field according to this invention may be applied during the time range from the initial sprouting time to the second leaf stage to third leaf stage of the weeds, and may be sprayed in a paddy field for the cultivation of paddy field rice during the time range before the implantation to 3 to 10 days after the implantation.

The present invention will now be described in detail by referring to examples thereof. However, it should be noted here that the invention is not limited only to the following examples.

Example 1

2',6'-Diethyl-N-[(2-cis-butenoxy)methyl]-2chloroacetanilide (hereinafter referred to as compound (1)) was prepared through the reactions shown by the following sequence of structural formula:

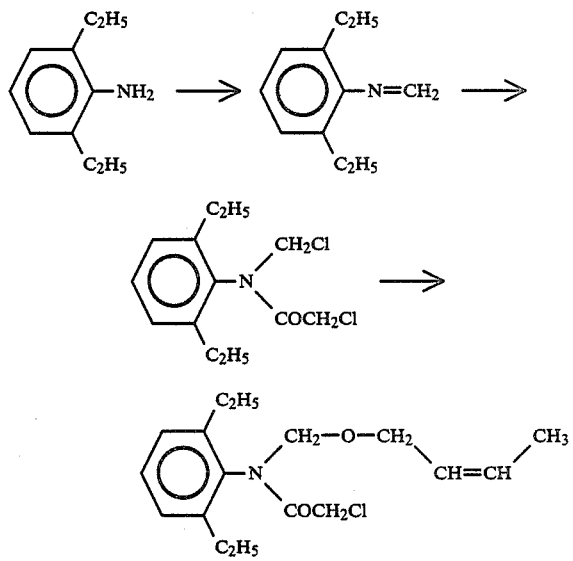

30.3 g of 2,6-diethylaniline, 35.1 g of a 38% formalin solution and 45 g of benzene were put into a 300 ml flask, and the content of the flask was refluxed on an oil bath for 4 hours. Then, the aqueous layer was removed, and the remaining oily layer was dehydrated by condensation to obtain 23.1 g of N-2,6-diethylphenyl-N-methyleneimine which was dissolved in 3.0 g of benzene and slowly added with 27.5 g of chloroacetylchloride dissolved in benzene while maintaining the reaction temperature at 0° C. After te completion of addition, the temperature of the reaction was raised to the room temperature. After stirring at the room temperature for 30 minutes, the reaction product was condensed using an evaporator to obtain 34.4 g of raw 2',6'-diethyl-N-chloromethyl-2-chloroacetanilide.

The thus obtained raw product was dissolved in 20 g of benzene, added with 14.2 g of 2-cis-butenol (content of cis-form isomer: 99%) and allowed to react by stirring the mixture at the room temperature for 4 hours. After the completion of reaction, 200 ml of water and 200 ml of ethyl ether were added. After stirring vigorously, the reaction mixture was allowed to stand still to separate an aqueous layer. The aqueous layer was discharged and the oily layer was washed with water repeatedly. Then, the oily layer was dehydrated by the addition of magnesium sulfate, and ether was evaporated. As a result, 10.2 g of the objected product was obtained in the form of dark yellow oil. The yield of the raw product was 94%.

The raw product was refined in a silica gel column using benzene as the eluent to obtain 5.3 g of a refined product in the form of light amber-colored oil.

The thus refined oily product was subjected to elemental analysis, IR'NMR and $^{13}$C-NMR to ascertain that the oily product was 2',6'-diethyl-N-[(2-cisbutenoxy)methyl]-2-chloroacetanilide (purity: 99%) contaminated with 1% of the by-product trans-isomer.

Elemental Analysis: $C_{17}H_{24}NO_2Cl$

|  | C | H | N | Cl |
|---|---|---|---|---|
| Calculated (%): | 65.90 | 7.81 | 4.52 | 11.44 |
| Found (%): | 65.64 | 7.98 | 4.92 | 11.71 |

IR $(cm^{-1})$: 1680 (—N—C(=O)—), 1080 (—O—)

H—NMR: 7.04 (3H, m), 5.39 (2H, m), 4.81 (2H, s)
4.15 (2H, d), 3.56 (2H, s), 2.56 (4H, q)
1.60 (3H, d), 1.20 (6H, t)

Refractive Index $(n_D^{25})$: 1.5256

The ratio between the cis- and trans-isomers contained in the product was determined by means of the $^{13}$C-NMR analysis In the $^{13}$C-NMR analysis, the chemical shift value was obtained firstly by using 2-cis- and 2-trans-butenol as the model compounds, and then the molar ratio between the cis- and trans-isomers of respective compounds (1), (2) and (B), the compound (1) being the objective compound of thi example and the compounds (2) and (B) being the objective compounds of the following examples, through the area-weight method while removing NOE effects by gated decoupling.

EXAMPLE 2

2',6'-diethyl-N-[(2-cis-pentenoxy)methyl]-2-chloroacetanilide (hereinafter referred to as compound (2)) was prepared generally in accordance with the procedures as described in Example 1, except in that 17.2 g of 2-cis-pentenol (content of cis-isomer: 99%) in place of 2-cis-butenol. 5.4 g of an oily product having an amber-color was obtained. The oily product was subjected to the analysis, similar to Example 1, to ascertain that the product was 2',6'-diethyl-N[(2-cis-pentenoxy)-methyl]-2-chloroacetanilide containing 99% of the cis-isomer.

Elemental Analysis: $C_{18}H_{26}NO_2Cl$

|  | C | H | N | Cl |
|---|---|---|---|---|
| Calculated (%): | 66.76 | 8.09 | 4.33 | 10.95 |
| Found (%): | 66.59 | 8.30 | 4.61 | 11.33 |

IR $(cm^-)$: 1680 (—N—C(=O)—), 1080 (—O—)

H—NMR: 7.20 (3H, m), 5.45 (2H, m), 4.97 (2H, d)
3.87 (2H, s), 2.52 (4H, q), 2.05 (2H, m)
1.22 (6H, t), 0.97 (3H, t)

Refractive index $(n_D^{25})$: 1.5216

REFERENCE EXAMPLE 1

Generally following to the procedures as described in Example 1, except in that n-butanol was used in place of 2-cis-butenol, whereby an amber-colored oily product was obtained. The oily product was analyzed by the analysis conducted similar to Example 1 to ascertain that the product was 2',6'-diethyl-N-butoxymethyl-2-chloroacetanilide (hereinafter referred to compound (A)).

REFERENCE EXAMPLE 2

Generally following to the procedures as described in Example 1, except in that 2-trans-butenol (content of trans-isomer: 95%) was used in place of 2-cis-butenol to obtain 5.2 g of an amber-colored oily product. The oily product was analyzed by the analysis conducted similar to Example 1 to ascertain that the product was 2',6'-diethyl-N-[(2-trans-butenoxy)methyl]-2-chloroacetanilide (content of trans-isomer: 94%, hereinafter referred to as compound (B)).

Elemental Analysis: $C_{17}H_{24}NO_2Cl$

|  | C | H | N | Cl |
|---|---|---|---|---|
| Calculated (%): | 65.90 | 7.81 | 4.52 | 11.44 |
| Found (%): | 65.58 | 7.92 | 4.76 | 11.82 |

IR (cm$^{-1}$): 1675 (—N—C(=O)—), 1909 (—O—), 965 (trans)

H—NMR: 7.20 (3H, m), 5.60 (2H, m), 4.82 (2H, s)
4.05 (2H, d), 3.68 (2H, s), 2.65 (4H, q)
1.63 (3H, d), 1.22 (6H, t)

Refractive index ($n_D^{25}$): 1.5218

For using the compounds of the present invention as a herbicide, various auxiliaries such as a diluting agent, solvent, surfactant and the like are blended therewith, and the blend thus obtained is prepared into a form such as an emulsion, wettable powder, dust, granules, etc.

For the purpose of reducing the labor in application, or of making the herbicide of the present invention effectively applicable for a wider range of types of weeds, there are cases where addition of other herbicides is appropriate.

The following are the examples of the chemicals that can be added thereto.

2,4-dichlorophenoxyacetic acid, and the salt, ester, and alkylamine salt thereof;
2-methyl-4-chlorophenoxyacetic acid, and the salt and ester thereof;
2-methyl-4-chlorophenoxybutyric acid, and the salt and ester thereof;
d,l-2-(4-chloro-O-tolyloxy)propionic acid, and the salt and ester thereof;
octanoic acid-4-cyano-2,6-diiodophenyl;
2,4-dichlorophenyl-4'-nitrophenyl ether;
2,4,6-trichlorophenyl-4'-nitrophenyl ether;
2,4-dichlorophenyl-3'-methoxy-4'-nitrophenyl ether;
3,4-dichlorocarbanilic acid methyl;
3-chlorocarbanilic acid isopropyl;
diethylthiocarbamic acid-S-4-chlorobenzyl;
4-nitrophenyl-3',5'-xylyl ether;
hexahydro-1H-azepine-1-carbothioic acid-S-ethyl;
3,4-dichloropropionanilide;
2',6'-diethyl-N-(butoxymethyl)-2-chloroacetanilide;
2',6'-diethyl-N-(n-propoxyethyl)-2-chloro-acetanilide;
2',6,-diethyl-N-(butoxyethyl)-2-chloroacetanilide;
1-(α,α-dimethylbenzyl)-3-p-tolylurea;
2,4-bis(ethylamino)-6-methylthio-1,3,5-triazine;
2-ethylamino-4-isopropylamino-6-methylthio-1,3,5-triazine;
2,4-bis(isopropylamino)-6-methylthio-1,3,5-triazine;
5-tert-butyl-3-(2,4-dichloro-5-isopropoxyphenyl) 1,3,4-oxadiazoline-2-on;
2,6-dichlorobenzonitrile;
2,6-dichlorothiobenzamide;
2-amino-3-chloro-1,4-naphthoquinone;
2,4-dichlorophenyl-3'-carbomethoxy-4'-nitrophenylether;
N-p-chlorobenzyloxyphenyl-3,4,5,6-tetrahydrophthalimide;
2,4-dichlorophenyl-3'-ethoxyethoxyethoxy-4'nitrophenyl ether;
N-(1-ethylpropyl)-2,6-dinitro-3,4-xylidine;
4-(2,4-dichlorobenzoyl)-1,3-dimethyl-pyrazole-5-yl-p-toluenesulfonate;
4-(2,4-dichlorobenzoyl)-1,3-dimethyl-5-(benzoylmethoxy)pyrazole;
O,O-diisopropyl-2-(benzenesulfonamide)ethylene dithiophosphate;
3,3'-dimethyl-4-methoxybenzophenone;
O-ethyl-0-(2-methyl-6-nitrophenyl) N-secbutylphosphorothioamidate;
3-isopropyl-2,1,3-benzothiaziazinone-(4)-2,2-dioxide and the salt thereof;
S-(2-methyl-1-piperidyl-carbonylmethyl)-O,O-di-n-propyldithiophosphate;
S-benzyl-N,N-dimethylthiocarbamate.

We hereinafter explain Preparation Examples of the compounds of the present invention, but the types of additives and the blending ratio are not limited to these Examples but may be varied over a broad range. "Part" in the respective Examples stands for part by weight.

PREPARATION EXAMPLE 1

Wettable powder 20 parts of the compound (1) of the present invention was mixed with 35 parts diatom earth, 40 parts talc, 3 parts lignin sodium sulfonate, and 2 parts dodecylbenzene sodium sulfonate, and the blend was then ground to obtain a wettable powder.

PREPARATION EXAMPLE 2

Granules 5 parts of the compound (2) of the present invention was uniformly mixed with 15 parts bentonite, 52.5 parts talc, 25 parts clay, 2 parts lignin sodium sulfonate, and 0.5 parts dodecylbenzene sodium sulfonate and ground. Then, with addition of water, the blend was granulated by an extrusion type granulator, and subjected to drying and sieving to form granules.

PREPARATION EXAMPLE 3

Emulsion 20 parts of the compound (1) of the present invention was uniformly dissolved with 73 parts xylene, 5 parts polyoxyethylene alkylether, 2 parts alkylbenzene calcium sulfonate to obtain an emulsion.

In application of the herbicidal composition of the present invention, the aforementioned essential ingredient compounds [A] and [B] or [A] and [C] are blended with various auxiliaries according to an ordinary agricultural chemical-preparing method, and prepared in such forms as granules, wettable powder and emulsion. And in this instance, the essential ingredient compounds may either be concurrently mixed and prepared into a final preparation, or separately prepared then blended together.

As the carrier or diluting agent, there can, for example, be used such inert solid carriers as clay, talc, bentonite, calcium carbonate, white carbon, etc., and such inert liquidcarriers as water or organic solvents, etc. For enhancing the biological effects or for improving the properties of the preparation products, nonionic, anionic or cationic surfactants or various high molecular compounds may be added as the auxiliaries. These auxiliaries are of course not limited to those mentioned above. "Part" in the following Blending Examples stands for part by weight.

EXAMPLE OF BLEND 1

3 parts of the compound A-1 and 7 parts of the compound B-1 were blended and ground with 25 parts clay, 1 part polyoxyethylene glycolcleyl ether and 1 part white carbon, and the blend thus obtained was mixed with 39 parts clay, 2 parts lignin sodium sulfonate, 2 parts dodecylbenzene sodium sulfonate, and 20 parts bentonite. The mixture obtained was then granulated by a granulator, and dried and sieved to obtain granules.

EXAMPLE OF BLEND 2

2.5 parts of the compound A-1 and 7 parts of the compound C-1 were uniformly mixed and ground with 15 parts bentonite, 48 parts talc, 25 parts clay, 2 parts lignin sodium sulfonate, and 0.5 part dodecylbenzene sodium sulfonate, and with addition of water, the blend was granulated by a granulator, and dried and sieved to obtain granules.

EXAMPLE OF BLEND 3

3 parts of the compound A-2 and 8 parts of the compound B-2 were mixed and ground with 15 parts white carbon, 2 parts condensate of naphthalene sodium sulfonate and formaldehyde, 5 parts polyoxyethylene alkylarylether sulfate and 67 parts clay to form a wettable powder.

Now, we hereinafter explain the effects of the compounds of the present invention referring to the test examples thereof.

It is quite evident from the results obtained that the compounds of the present invention have excellent pharmaceutical effects as compared with the compounds (A) and (B) described in Comparative Examples 1 and 2, and that they inflict less chemical injury to paddy field rice plants.

In the Tables in the following Test Examples, (i)–(viii) represent the following weeds:
(i): *Eohinoohloa crus-galli P. Beauv.*
(ii): *Callitriche verna L.*
(iii): *Potala indica Koehne*
(iv): *Cyperus microiria Steud.*
(v): *Monochoria vaginalis Presl.*
(vi): *Scirpus hotarui Ohwi*
(vii): *Sagittaria pygmaea Miq.*
(viii): *Dopatrium junceum Hamilt.*

TEST EXAMPLE 1

*Echinochloa crus-galli P. Beauv-Control* Test in Direct-sown Flooded Paddy Field Paddy field soil was placed in Wagner pots of 1/5000 are, and after puddling and levelling the beds, 20 grains of paddy field rice plant seed (Type: "Nipponbare") and 50 grains of *Echinochloa crus-galli P. Beauv.* seed were sown therein. When the paddy field rice plant seed and the *Echinochloa crus-galli P. Beauv.* seed had germinated and 10 days had elapsed after sowing (the first leaf stage), the depth of the covering water was adjusted to 3 cm, and the compound of the present invention, granulated according to the Preparation Example 2 and measured up to the designated amount, was uniformly applied over the water surface.

Fourteen days afer the chemical treatment, the weed-killing effect and the effect on the rice plant were investigated. The results were as shown in Table 1.

TABLE 1

| Compound | | Amount of ingredient g/a | Treatment of germinating stage (i) | Treatment of germinating stage Rice plant | Treatment in first-leaf stage (i) | Treatment in first-leaf stage Rice plant |
|---|---|---|---|---|---|---|
| Chemicals of present invention | (1) | 10 | 0 | 67 | 0 | 98 |
| | | 2.5 | 0 | 100 | 0 | 100 |
| | | 0.625 | 0 | 100 | 0 | 100 |
| | (2) | 10 | 0 | 100 | 0 | 100 |
| | | 2.5 | 0 | 100 | 0 | 100 |
| | | 0.625 | 16 | 100 | 48 | 100 |
| Comparative Chemicals | (A) | 10 | 0 | 43 | 0 | 57 |
| | | 2.5 | 0 | 86 | 0 | 86 |
| | | 0.625 | 13 | 93 | 83 | 100 |
| | (B) | 10 | 0 | 32 | 0 | 46 |
| | | 2.5 | 0 | 55 | 24 | 89 |
| | | 0.625 | 58 | 97 | 100 | 100 |
| Untreated plot | | — | 100 | 100 | 100 | 100 |

(The values denote the ratio of living plant by weight to that for the untreated plot.)

TEST EXAMPLE 2

Test of Treating Soil against Weeds in Paddy Field

Paddy field soil was placed in Wagner pots of 1/5000 are and four young seedlings of paddy field rice plant in the second-leaf stage, (about 10 cm tall), (Type: "Nipponbare"), were transplanted per pot. Soil containing a large amount of seeds of *Echinochloa crusgalli P. Beauv.* and other major paddy field weeds was uniformly introduced within 2 cm depth of the surface layer. The soil was then covered with water up to a depth of 3 cm. When *Echinochloa crus-galli P. Beauv.* had grown to near the first-leaf stage, the emulsion of the compound of the present invention, prepared according to the Preparation Example 3 and diluted with a designated amount of water, was uniformly sprinkled, and the pot was maintained at an average temperature of 28° C. Twenty-five days after the sprinkling of the chemical, the weed-killing effect and the chemical injury to the paddy field rice plant were investigated. Table 2 shows the results obtained. The effect and the chemical injury to the rice plant were evaluated according to the following six stages.

5: Weed-killing rate relative to the untreated plot more than 80% (Rate of chemical injury to rice plant relative to the untreated plot)
4: Weed-killing rate relative to the untreated plot 60–79% (Rate of chemical injury to rice plant relative to the untreated plot)
3: Weed-killing rate relative to the untreated plot 40–59% (Rate of chemical injury to rice plant relative to the untreated plot)
2: Weed-killing rate relative to the untreated plot 20–39% (Rate of chemical injury to rice plant relative to the untreated plot)
1: Weed-killing rate relative to the untreated plot less than 20% (Rate of chemical injury to rice plant relative to the untreated plot)
0: Entirely the same as the untreated plot.

TABLE 2

| Compound | | Amount of ingredient g/a | Effects of Chemicals | | | | | | Chemical injury to water-field rice plant |
|---|---|---|---|---|---|---|---|---|---|
| | | | (i) | (ii) | (iii) | (iv) | (v) | (vi) | |
| Chemicals of present invention | (1) | 10 | 5 | 5 | 5 | 5 | 5 | 4–5 | 0 |
| | | 2.5 | 5 | 5 | 5 | 5 | 5 | 4–5 | 0 |
| | | 0.625 | 5 | 5 | 5 | 5 | 5 | 4–5 | 0 |
| | (2) | 10 | 5 | 5 | 5 | 5 | 5 | 4–5 | 0 |
| | | 2.5 | 5 | 5 | 5 | 5 | 5 | 4–5 | 0 |
| | | 0.625 | 4–5 | 4–5 | 5 | 5 | 4 | 4 | 0 |
| Comparative chemicals | (A) | 10 | 5 | 5 | 5 | 5 | 5 | 4–5 | 2 |
| | | 2.5 | 5–4 | 4 | 5 | 5 | 5 | 4–5 | 1 |
| | | 0.625 | 3 | 2 | 2 | 5 | 5 | 3 | 0 |
| | (B) | 10 | 5 | 5 | 5 | 5 | 5 | 4–5 | 2 |
| | | 2.5 | 3–4 | 4 | 5 | 5 | 5 | 3–4 | 2 |
| | | 0.625 | 2 | 2 | 2 | 4 | 5 | 2 | 0 |
| Untreated plot | | — | 0 | 0 | 0 | 0 | 0 | 0 | 0 |

TEST EXAMPLE 3

Blend Proportion of Compound (1) and Compound (B), and Weed-killing Effect

By entirely the same method as Test Example 2, *Echinochloa crus-galli P. Beauv.* in one and half-leaf stage (in case of annual, broad-leaf weeds, at the initial stage of main leaf-development, and in case of Scirpus hotarui Ohwi, in the second-leaf stage) was treated with the respective chemicals in each designated concentration, and twenty days after the treatment, two weed-killing effect was investigated. The method of evaluation was the same as Test Example 2. Table 3 shows the results obtained.

TABLE 3

| Compound (mol % of cis-form) | Amount of ingredient g/a | Effects of Chemicals | | | | | |
|---|---|---|---|---|---|---|---|
| | | (iii) | (ii) | (iv) | (vi) | (vii) | (i) |
| (1) | 1.6 | 5 | 5 | 5 | 4–5 | 2 | 5 |
| (99%) | 0.4 | 5 | 5 | 5 | 3 | 2 | 5 |
| | 0.1 | 3 | 3 | 4 | 1 | 1 | 2 |
| 3:1 mixture of (1) and (B) (76%) | 1.6 | 5 | 5 | 5 | 4 | 2 | 5 |
| | 0.4 | 4 | 4 | 5 | 1 | 2 | 4 |
| | 0.1 | 2 | 2 | 4 | 1 | 1 | 1 |
| 1:3 mixture of (1) and (B) (29%) | 1.6 | 4 | 4 | 4 | 3 | 2 | 4–5 |
| | 0.4 | 3 | 2 | 4 | 1 | 1 | 2 |
| | 0.1 | 1 | 1 | 3 | 1 | 1 | 1 |
| (B) (6%) | 1.6 | 4 | 3–4 | 4 | 2 | 1 | 3 |
| | 0.4 | 2 | 2 | 4 | 1 | 1 | 2 |
| | 0.1 | 1 | 1 | 2 | 1 | 1 | 1 |
| Untreated plot | — | 0 | 0 | 0 | 0 | 0 | 0 |

*Values calculated from the cis-trans proportions of compounds (1) and (B)

TEST EXAMPLE 4 Test of Toxicity for Fish

In case of Comparative Chemical (A), the fatal concentration killing half the number of carp (born that year) (Median Tolerance Limit, TLM) 48 hours after the treatment was 0.6 ppm while the compound (1) of the present invention indicated a TLM value 1 ppm; thus the latter was confirmed to be safer for fish.

Hereinafter, we explain the effects of the herbicidal composition of the present invention.

TEST EXAMPLE 5

Paddy field soil was placed in Wagner pots of 1/5000 are, and after covering with water, the seed of *Echinochloa crus-galli P. Beauv.* was sown 50 grains per pot. When the *Echinochloa crus-galli P. Beauv.* had grown to the first-leaf stage, it was treated with the sample chemicals, prepared to provide the amount of chemical in a designated concentration according to Blend Example 2. Twenty days after treating with the chemical, the remaining weeds were pulled, and their air-dried weight was measured, then the percentage relative to the untreated plot was calculated to obtain the percentage weeds rest in weight. The results are shown in Table 4.

TABLE 4

| Weeds Rest in Weight of *Echinochloa crus-galli* P. Beauv. (%) | | | | | | |
|---|---|---|---|---|---|---|
| Amount of compound B-1 used in treatment g/a | Amount of compound A-1 used in Treatment g/a | | | | | |
| | 0 | 0.25 | 0.5 | 1 | 2 | 4 |
| 0 | 100 | 68 | 18 | 0 | 0 | 0 |
| 0.25 | 98 | 37 | 5 | 0 | 0 | 0 |
| 0.5 | 86 | 26 | 0 | 0 | 0 | 0 |
| 1.0 | 65 | 18 | 0 | 0 | 0 | 0 |
| 2.0 | 39 | 2 | 0 | 0 | 0 | 0 |
| 4.0 | 15 | 0 | 0 | 0 | 0 | 0 |

When the results shown in Table 4 are analyzed according to Colby Method "Weeds" Vol. 15, pp. 20–22, 1967), assuming the percentage weeds rest in weight in case where p g/a of compound [A] is used to be X % and the percentage weeds rest in weight in case where q g/a of compound [B] is used to be Y%, the percentage weeds rest in weight (E) that is estimated for the case where compound [A] and compound [B] are used together in each p g/a and q g/a, can be obtained by the following formula:

$$(E) = X \cdot Y / 100$$

When the actual percentage weeds rest in weight is lower than the calculated value (the estimated value), it is judged that there is a synergistic effect. The percentage weeds rest in weight (E) actually obtained in this Test was much lower than the calculated value, and it was confirmed that there were unexpected synergistic effects.

TEST EXAMPLE 6

Paddy field soil was placed in Wagner pots of 1/5000 are, and after covering with water, the rootstalks of *Sagittaria pygmaea Miq.* were planted and grown. When *Sagittaria pygmae Miq.* reached the second-leaf stage, they were treated with the sample chemical, prepared to have a designated concentration according to Blend Example 2. Thirty days after treating with the chemical, the remaining *Sagittaria pygmae Miq.* were pulled, and the percentage weeds rest in weight was obtained in the same way as in Test Example 5, and thereby the results as shown in Table 5 were obtained.

TABLE 5

| Active ingredient compound | Amount of active ingredient g/a | Weeds rest in weight % |
|---|---|---|
| A-1 | 0.5 | 98 |
| " | 1 | 85 |
| " | 2 | 42 |
| A-2 | 0.5 | 100 |
| " | 1 | 87 |
| " | 2 | 70 |
| B-1 | 3 | 64 |
| " | 6 | 15 |
| " | 12 | 0 |
| B-2 | 3 | 65 |
| " | 6 | 8 |
| " | 12 | 0 |
| [C]-1 | 3 | 82 |
| " | 6 | 40 |
| " | 12 | 0 |
| A-1/B-1 | 0.5/2 | 0 |
| " | 0.5/3 | 0 |
| " | 1/6 | 0 |
| " | 2/12 | 0 |
| A-2/B-2 | 0.5/2 | 21 |
| " | 0.5/3 | 12 |
| " | 1/6 | 0 |
| " | 2/12 | 0 |
| A-1/[C]-1 | 0.5/2 | 0 |
| " | 0.5/3 | 0 |
| " | 1/6 | 0 |
| " | 2/12 | 0 |
| A-1/B-2 | 0.5/2 | 0 |
| " | 0.5/3 | 0 |
| " | 1/6 | 0 |
| " | 2/12 | 0 |

TEST EXAMPLE 7

Paddy field soil was placed in Wagner pots of 1/5000 are, and soil containing a large amount of seeds of *Echinochloa crus-galli P. Beauv.* and other major paddy field weeds was uniformly introduced within 2 cm depth of the surface layer, whereafter covering water was applied to a depth of 3 cm. The rootstalks of *Sagittaria pygmaea Miq.* were also planted. Then young seedlings of paddy field rice plant (Type: "Nipponbare", seedlings in the 2.5-leaf stage) were transplanted and grown therein. Ten days after transplantation, in the initial stage of weed-growing, the treatment was carried out with a designated amount of the sample chemical. Twenty-five days after the chemical sprinkling, the weed-killing effect and the chemical injury to the paddy field rice plant were evaluated in the six stages described in Test Example 2.

TABLE 6

| Test sample compound | Amount of active ingredient % | Weed-killing effects | | | | | | | Chemical injury to rice plant |
|---|---|---|---|---|---|---|---|---|---|
| | | (iii) | (ii) | (viii) | (iv) | (vi) | (i) | (vii) | |
| A-1 | 2 | 5 | 5 | 5 | 5 | 4 | 5 | 1 | 0 |
| | 1 | 3 | 3 | 5 | 3 | 3 | 4 | 1 | 0 |
| | 0.5 | 1 | 1 | 1 | 3 | 1 | 2 | 0 | 0 |
| B-1 | 12 | 5 | 5 | 5 | 5 | 4 | 2 | 5 | 0 |
| | 6 | 4 | 3 | 5 | 3 | 2 | 1 | 3 | 0 |
| | 3 | 3 | 3 | 4 | 2 | 1 | 1 | 2 | 0 |
| B-2 | 12 | 5 | 5 | 5 | 5 | 4 | 2 | 5 | 0 |
| | 6 | 3 | 3 | 5 | 3 | 2 | 1 | 3 | 0 |
| | 3 | 3 | 2 | 4 | 2 | 1 | 1 | 2 | 0 |
| B-3 | 12 | 5 | 5 | 5 | 5 | 5 | 2 | 5 | 0 |
| | 6 | 4 | 3 | 5 | 3 | 3 | 1 | 3 | 0 |
| | 3 | 3 | 2 | 4 | 2 | 1 | 1 | 2 | 0 |
| [C] | 12 | 5 | 5 | 5 | 5 | 5 | 2 | 5 | 1 |
| | 6 | 5 | 5 | 5 | 3 | 4 | 1 | 3 | 0 |
| | 3 | 3 | 3 | 5 | 1 | 1 | 0 | 1 | 0 |
| A-1/B-1 | 2/12 | 5 | 5 | 5 | 5 | 5 | 5 | 5 | 0 |
| | 1/6 | 5 | 5 | 5 | 5 | 5 | 5 | 5 | 0 |
| | 0.5/3 | 5 | 5 | 5 | 5 | 3 | 5 | 3 | 0 |
| A-1/B-2 | 2/12 | 5 | 5 | 5 | 5 | 5 | 5 | 5 | 0 |
| | 1/6 | 5 | 5 | 5 | 5 | 5 | 5 | 5 | 0 |
| | 0.5/3 | 5 | 5 | 5 | 5 | 3 | 5 | 3 | 0 |
| A-1/B-3 | 2/12 | 5 | 5 | 5 | 5 | 5 | 5 | 5 | 0 |
| | 1/6 | 5 | 5 | 5 | 5 | 5 | 5 | 5 | 0 |
| | 0.5/3 | 5 | 5 | 5 | 5 | 4 | 5 | 3 | 0 |
| A-1/[C] | 2/12 | 5 | 5 | 5 | 5 | 5 | 5 | 5 | 1 |
| | 1/6 | 5 | 5 | 5 | 5 | 5 | 5 | 5 | 0 |
| | 0.5/3 | 5 | 5 | 5 | 5 | 4 | 5 | 4 | 0 |
| Comparative composition D/B-1 | 2/12 | 5 | 5 | 5 | 5 | 5 | 5 | 5 | 1 |
| | 1/6 | 5 | 5 | 5 | 5 | 4 | 4 | 4 | 0 |
| | 0.5/3 | 5 | 4 | 5 | 5 | 3 | 3 | 2 | 0 |
| Comparative composition D/[C] | 2/12 | 5 | 5 | 5 | 5 | 5 | 5 | 5 | 2 |
| | 1/6 | 5 | 5 | 5 | 4 | 4 | 4 | 4 | 1 |
| | 0.5/3 | 5 | 4 | 5 | 2 | 2 | 3 | 2 | 0 |

(Remark) D stands for 2′,6′-diethyl-N—(butoxymethyl)-2-chloroacetanilide

The above Examples are to illustrate this invention. It should be understood that it is possible to give various changes without deviation from the scope indicated by the above Examples and specified in the claims.

We claim:

1. A herbicide for paddy fields containing 2/, 6/-diethyl-N-[(2-cis-butenoxy) methyl]-2-chloroacetanilide represented by the formula

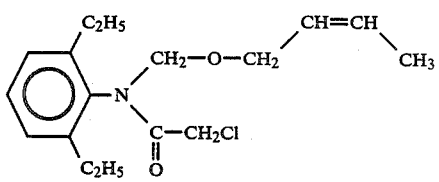

as its active ingredient.

2. A herbicide composition for paddy fields containing 2/, 6/- diethyl-N- [(2-cis-butenoxy) methyl]-2-chloro-acetanilide and 1,3-dimethyl-4-(2,4-dicholorobenzoyl) -5-pyrazolyl-4-toluenesulfonate as its active components.

3. A herbicidal composition for paddy fields ontaining 2/,6/-diethyl-N- [(2-cis-butenoxy) methyl]-2-chloroacetnilide and /-(2-naphthoxy)-propionanilide as its active components.

* * * * *